March 21, 1933. A. CUMMING, JR Plant Pat. 58
CHRYSANTHEMUM
Filed Nov. 17, 1932
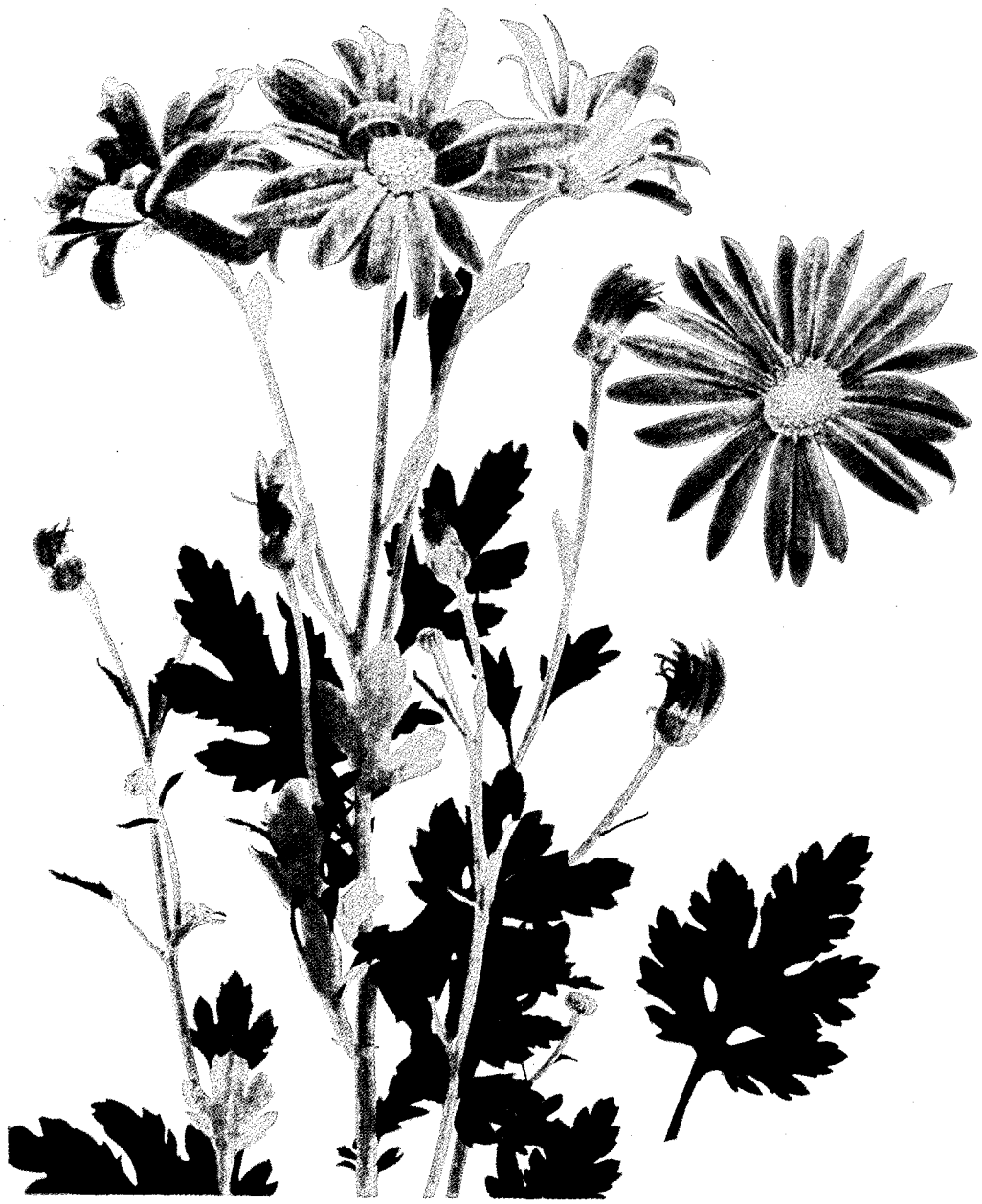
INVENTOR
Alexander Cumming Jr
By Orville M. Kile
PLANT PATENT AGENT Patented Mar. 21, 1933

Plant Pat. 58

UNITED STATES PATENT OFFICE

ALEXANDER CUMMING, JR., OF BRISTOL, CONNECTICUT, ASSIGNOR TO BRISTOL NURSERIES, INC., OF BRISTOL, CONNECTICUT

CHRYSANTHEMUM

Application filed November 17, 1932. Serial No. 643,105.

My invention relates to improvements in perennial chrysanthemums. This new chrysanthemum is a third generation hybrid from *Chrysanthemum Coreanum* crossed with *C. Hortorum*. It is distinct in habits of growth, shape of leaves, and in color of flowers. This new variety first attained sufficient size and bloom to show its superior qualities in October 1931. Since that time it has been reproduced from cuttings.

The accompanying illustration shows a flowering branch with buds and foliage. At the right is a full front view of a flower and a typical leaf. All are in approximately true natural colors, but it must be understood that there will be slight variations depending upon soil and climatic conditions, age of flower, etc.

The following is a detailed description of this new chrysanthemum:

*Habits of growth.*—This plant is a vigorous grower and bloomer, producing a growth of about two feet in one year. It sends up several stems from each base and these produce numerous wiry laterals, each of which branch still further and each small branch terminates in a bud. Thus large masses of blossoms are produced on each plant at one time, but there is a succession of blossoms over a considerable period, due to the tendency to send out many side shoots from the flowering branches. In general the growth resembles that of the Coreanum parent.

*Flowers.*—Single, two and one-half of three inches in diameter; petals one and one-half inches long and one-quarter inch wide; averaging thirty petals to a flower. The general color tone of the flower is approximately "nopel red" (Plate I, Ridgeway's Color Standards and Nomenclature) but with lighter slightly coppery effect toward the center and a considerably darker, almost "ox blood red" effect toward the tips of the petals.

The center of the flower consists of 115 to 120 separate pollen bearing cells, surrounded by 100 or more yellow anthers. The color effect of the center of the flower changes from green to yellow as the flower matures.

The flowers of this new variety possess the quality of remaining fresh and natural in color for an exceedingly long period after being cut and placed in water.

*Odor.*—The flower has a faint but sweet odor but it is not pungent like that of the Hortorum variety.

*Sepals.*—About 30 in number, arranged in two overlapping rows, each sepal being bright green and having brown membrane-like edges near the top. Just below the calyx, often within $\frac{1}{16}$ inch but sometimes $\frac{1}{4}$ inch, there is an additional sepal-like growth, probably a rudimentary leaf.

*Stems.*—Of a wiry nature, light green in color with a grayish overlay arising from a hair-like tracery over the entire surface of the stems.

*Leaves.*—"Elm green" (Plate XVII Ridgeway's Color Standards and Nomenclature) and of a shape readily distinguished from either Hortorum or Coreanum leaves, this new variety being about midway between the large, moderately cut Hortorum leaf and the small, depely cut Coreanum leaf.

I claim:

The variety of perennial chrysanthemum as shown and described, characterized particularly by its profusion of single flowers of a "nopal red" to "ox blood red" color, and by its distinctive foliage.

In testimony whereof I affix my signature.

ALEXANDER CUMMING, JR.